(12) United States Patent
Olivier

(10) Patent No.: US 7,943,372 B2
(45) Date of Patent: May 17, 2011

(54) MICROBIOLOGICAL TEST DEVICE, ASSEMBLY AND METHOD

(75) Inventor: Stephane Olivier, Rosheim (FR)

(73) Assignee: Millipore Corporation, Billerica, MA (US)

( * ) Notice: Subject to any disclaimer, the term of this patent is extended or adjusted under 35 U.S.C. 154(b) by 1028 days.

(21) Appl. No.: 11/805,540

(22) Filed: May 23, 2007

(65) Prior Publication Data

US 2008/0090285 A1 Apr. 17, 2008

(30) Foreign Application Priority Data

Jun. 1, 2006 (FR) ...................................... 06 52001

(51) Int. Cl.
*C12M 1/34* (2006.01)
*C12M 1/12* (2006.01)

(52) U.S. Cl. ............... 435/308.1; 435/297.2; 435/297.5; 422/534; 210/406; 210/416.1

(58) Field of Classification Search .................... None
See application file for complete search history.

(56) References Cited

U.S. PATENT DOCUMENTS

| | | | | |
|---|---|---|---|---|
| 2,923,669 | A * | 2/1960 | Poitras | 435/34 |
| 6,358,730 | B1 * | 3/2002 | Kane | 435/297.5 |
| 6,688,476 | B2 * | 2/2004 | Breillatt et al. | 210/435 |
| 2003/0228705 | A1 * | 12/2003 | Chan et al. | 436/177 |

FOREIGN PATENT DOCUMENTS

| | | |
|---|---|---|
| EP | 0 319 701 | 6/1989 |
| FR | 2 582 960 | 12/1986 |
| FR | 2 677 664 | 12/1992 |
| FR | 2 802 942 | 6/2001 |
| WO | 99/47637 | 9/1999 |

OTHER PUBLICATIONS

The French Search Report dated Mar. 12, 2007.

* cited by examiner

*Primary Examiner* — William H Beisner
(74) *Attorney, Agent, or Firm* — Nields, Lemack & Frame, LLC

(57) ABSTRACT

The device for microbiological testing of a sample of liquid includes an envelope and a filter membrane, the envelope including a removable body and a support for the membrane in the wetted state; the support including a sponge and the removable body including a flexible wall adapted to move toward the membrane, when the device is subjected to a reduced pressure and to return to its initial position when the reduced pressure ceases. The assembly includes a device of the above kind and a clamp adapted to grip the device in the manner of a vise. The method includes the step of obtaining such a device, of passing the sample between the inlet aperture and the outlet aperture of the device, of subjecting the device to a reduced pressure, of making the reduced pressure cease, and then of detecting the presence of microorganisms on the membrane of the device.

19 Claims, 8 Drawing Sheets

MICROBIOLOGICAL TEST DEVICE, ASSEMBLY AND METHOD

The present invention relates to the microbiological testing of a sample of liquid flowing under pressure.

Devices for microbiological testing of liquid samples under pressure including a microporous membrane through which the liquid under pressure is filtered are already known, in particular from French patent 2 802 942. These devices include an envelope formed from an inlet body having an inlet aperture and a cup adapted to receive the liquid entering via the inlet aperture before it is filtered through the membrane, and also from a drainage body separate from the inlet body, on the side opposite the cup and having a filtered liquid outlet aperture.

The drainage body includes a support pad against which the whole of the surface of the membrane rests in the wetted state (when it is impregnated with liquid).

This pad is rigid to support the membrane when it is wetted and to avoid the filtration pressure tearing it and is porous so that the liquid can be drained through the pad to the outlet aperture of the drainage body.

When all of the liquid has been filtered under pressure through the membrane of the device, the remaining liquid is then purged, for example by creating a reduced pressure in the device by means of a vacuum flask connected to the filter device via the outlet aperture.

The invention aims to provide a microbiological test device that is both simpler and more convenient to use, while minimizing the risk of contamination and ensuring optimum containment of microorganisms collected on the membrane.

To this end it provides a device for microbiological testing of a sample of liquid flowing under pressure, including an envelope and a filter membrane inside said envelope, said membrane subdividing the internal volume of said envelope into a liquid receiving volume communicating with an inlet aperture, and into a liquid drainage volume communicating with an outlet aperture, said envelope including a removable body and, inside said drainage volume, means for supporting said membrane when wetted;
characterized in that:
said support means include a relatively absorbent and flexible sponge; and
said removable body includes a flexible wall disposed against said sponge, said flexible wall being adapted to be moved toward said membrane when said device is subjected to a reduced pressure inside said drainage volume and to return to its initial position when said reduced pressure ceases.

In the prior art filter device mentioned above, the rigid and porous pad has the two-fold function of supporting the membrane and draining the liquid. This pad stores a large quantity of liquid that it is impossible to eliminate even by applying a strong vacuum to the downstream side of the device.

This is because, when the downstream side of the filter unit is subjected to a vacuum when purging the liquid, some of the liquid is aspirated and drained out of the device, until, when most of the liquid has been purged, the surfaces of the membrane come into contact with air.

In this situation, the membrane then behaves like an airtight film, no gas bubbles being able to escape from the pores of the wetted membrane (bubble point phenomenon).

Under these conditions, the reduced pressure applied at the outlet of the device is unable to drain from the filter device excess residual liquid contained in the membrane and in the device.

Moreover, in conventional filter devices, during the purging phase, the liquid is expelled to the outlet aperture along preferential paths leaving regions here and there that cannot be purged. The shape, area and configuration of these regions are strongly dependent on the losses of charge, the flows at the membrane of the device, and the relative position of the inlet and outlet apertures of the filter unit.

This phenomenon has the drawback of not being repeatable because of the unstable nature of the purging operation (random appearance of preferential paths, heterogeneous membranes, variability linked to the level of vacuum applied).

The operation of purging the liquid is therefore imperfect for this reason also.

In the device of the invention, the conjoint use of a sponge and a flexible wall makes it possible to absorb residual liquid that it has not been possible to eliminate.

Thus, in a first phase, when a reduced pressure is applied to the drainage volume of the device, the movement of the flexible wall toward the membrane squeezes the sponge impregnated with liquid between that wall and the membrane to expel from the sponge to the outlet aperture some of the liquid that it has absorbed, then, in a second phase, when the pressure inside the device returns to normal, the flexible wall returning to its initial position releases the sponge so that it expands and resumes a capacity for absorption enabling it to collect the residual liquid contained in the membrane and in the device, in particular neighboring the preferential liquid flow paths.

When the sponge has absorbed this residual liquid, the sponge and the flexible wall can be detached from the remainder of the envelope to obtain access to the membrane.

The liquid contained in the pores of the membrane of the device is therefore purged more effectively, with the result that the membrane is emptied of most of its water, any moisture remaining in the membrane being distributed homogeneously over the whole of its surface, which ensures optimum conditions for subsequently, for example, growing any microorganisms collected on the membrane, or for fast detection of the microorganisms by spraying a reagent onto the membrane (with no risk of excessively diluting the reagent).

Features preferred for reasons of simplicity, convenience and economy of implementation and use include:
said support means also include a porous sintered and relatively rigid member disposed between said membrane and said sponge.

Adding the relatively rigid porous sintered member reinforces the mechanical support of the membrane with the result that high filter pressures can be achieved without marking or deforming the membrane.

According to other features that are preferred for the same reasons as above:
said sponge is of polyvinylacetate;
said removable body of said envelope is formed of said flexible wall;
said flexible wall is a peelable film;
said film is of polyethylene;
said flexible wall holds said support means in position inside said envelope;
said flexible wall is sealed to said support means;
said device includes a first calibrated valve disposed between said inlet aperture and said receiving volume and a second calibrated valve disposed between said drainage volume and said outlet aperture, said valves being adapted to open in the direction of flow from said inlet aperture to said outlet aperture;

a vent adapted to allow air to pass between the interior and the exterior of said envelope is formed in said envelope; and/or said membrane, said sponge and said peelable film have closed contours.

A second aspect of the invention consists in an assembly for microbiological testing of a sample of liquid flowing under pressure including a device as set forth above and a clamp having clamping means adapted to hold said device in the manner of a vise by said flexible wall.

Thus pressure stresses exerted on the device are thus mechanically absorbed by the clamp.

Unlike the disposable device, the clamp can be used again for each new device and enables the device to resist high flow pressures.

According to features that are preferred for reasons of simplicity and convenience as much manufacture as of use:

said clamp has a fixed plate and a plate mobile between a rest position in which it is away from the device and a clamping position in which it bears against said device.

According to other features that are preferred for the same reasons as above:

the plate that bears on said flexible wall has a central cavity and said flexible wall of said device is also adapted to move away from said membrane within said cavity when said device is subjected to an increased pressure in said drainage volume and to return to its initial position when said increased pressure ceases.

During filtering, the increased pressure generated in the drainage volume causes the flexible wall to move away from the membrane, which increases the drainage volume by occupying a portion of the space of the cavity of the clamp provided for this purpose and thereby facilitates the flow of the liquid toward the outlet aperture.

According to a third aspect, the invention also relates to a method for the microbiological testing of a sample of liquid flowing under pressure including:

a) the step of obtaining a device as set forth above;
b) the step of passing said sample between the inlet aperture and the outlet aperture of said device;
c) the step of subjecting said device to a reduced pressure within the drainage volume of said device;
d) the step of making said reduced pressure cease; then
e) the step of detecting the presence of microorganisms on the membrane of said device.

According to preferred features, for reasons of simplicity and convenience of use:

the method further includes, prior to step e), the step of passing a rinsing liquid between the inlet aperture and the outlet aperture of said device and then the implementation of steps c) and d) again;

the method further includes, prior to step e), the step of passing a nutritive liquid between the inlet aperture and the outlet aperture of said device and then the implementation of steps c) and d) again;

the method further includes, prior to step e), the step of passing between the inlet aperture and the outlet aperture of said device a liquid adapted to reveal the presence of microorganisms by luminescence and then the implementation of steps c) and d) again; and/or the method includes, prior to step e), the step of repeating steps c) and d) at least once.

The explanation of the invention continues with the DETAILED DESCRIPTION of one embodiment of the invention given hereinafter by way of illustrative and nonlimiting example and with reference to the appended drawings. In the drawings.

Figure 1:
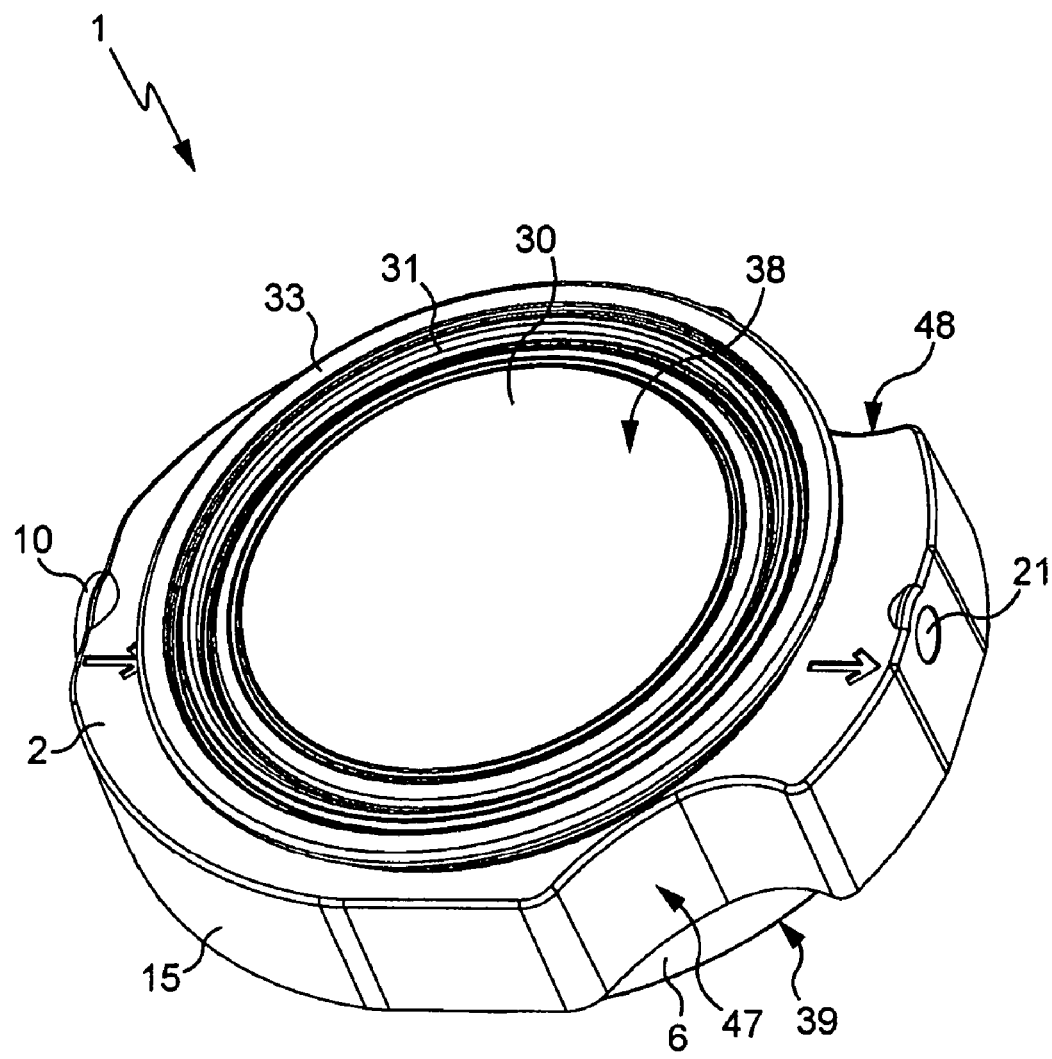
FIG. 1 is a perspective view of a microbiological test device of the invention.
Figure 2:
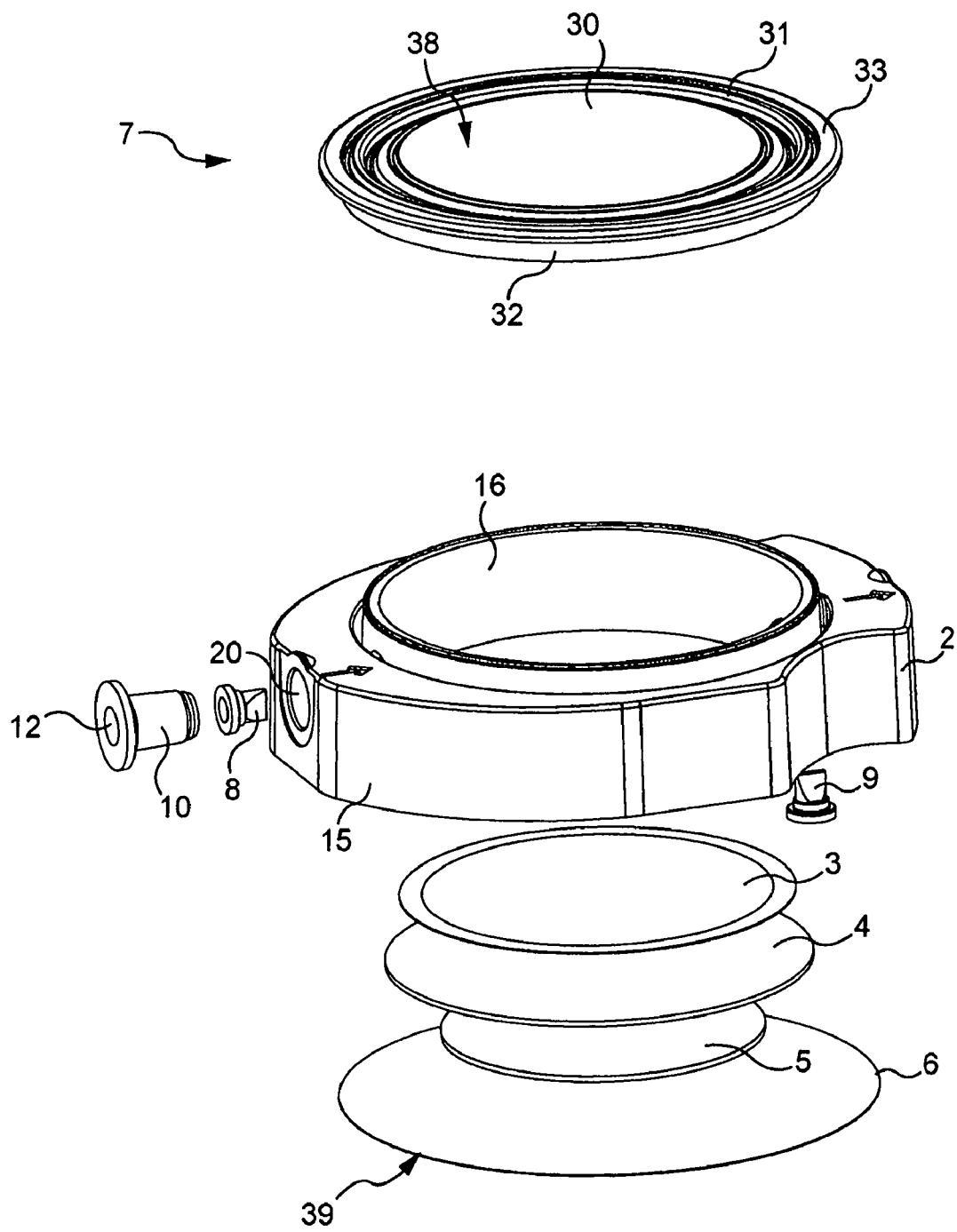
FIG. 2 is a similar view of the device but in an exploded presentation.
Figure 3:
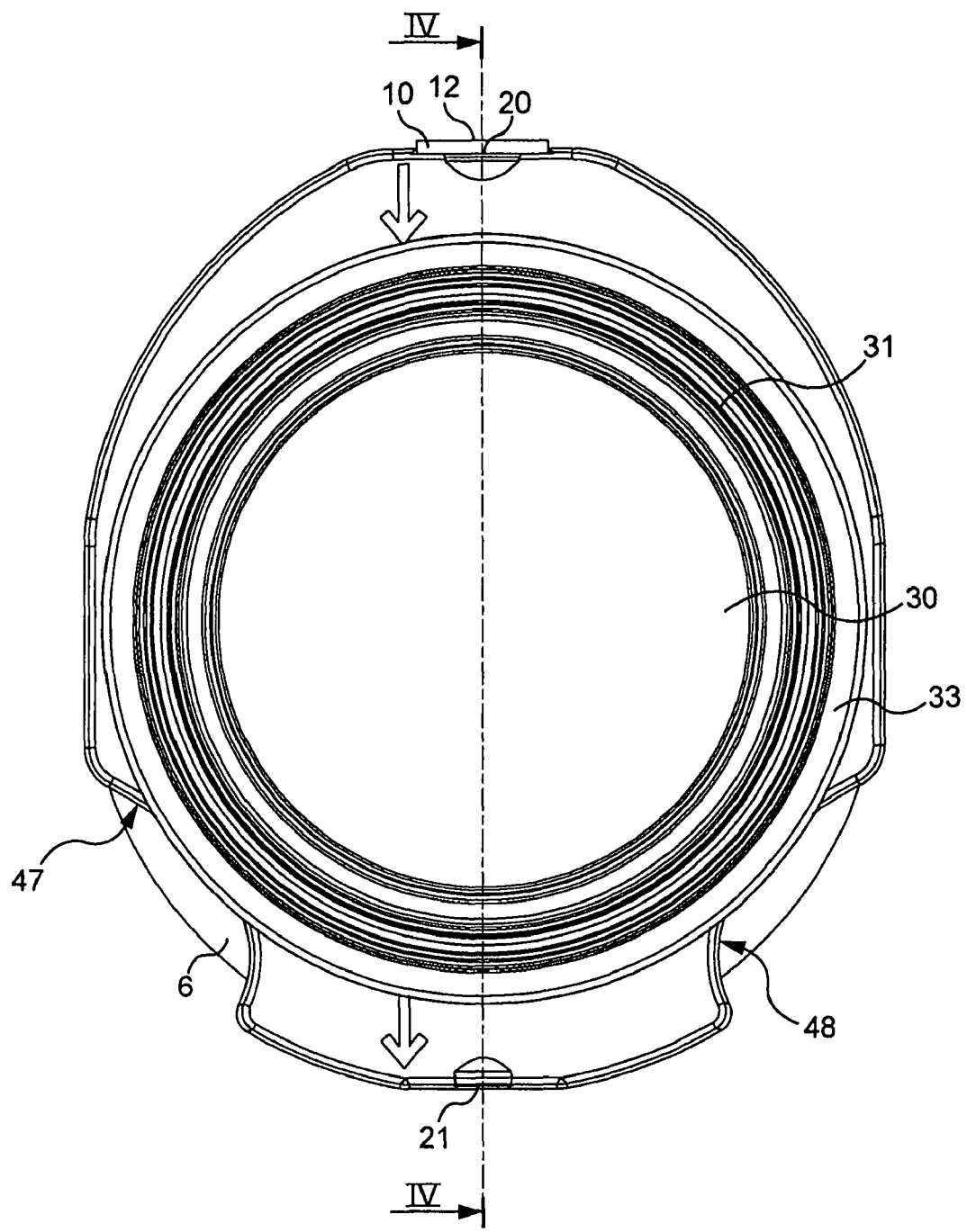
FIG. 3 is a top plan view of the device.

The microbiological test device 1 represented in FIGS. 1 to 3 includes a body 2, a membrane 3, a porous sintered member 4, a disk-shaped sponge 5, a peelable plastic film 6 and a cover 7.

The body 2, the plastic film 6 and the cover 7 form an envelope 11 inside which the membrane 3 is situated.

The device also includes two check valves 8 and 9 and a female insert 10.

Figure 5:
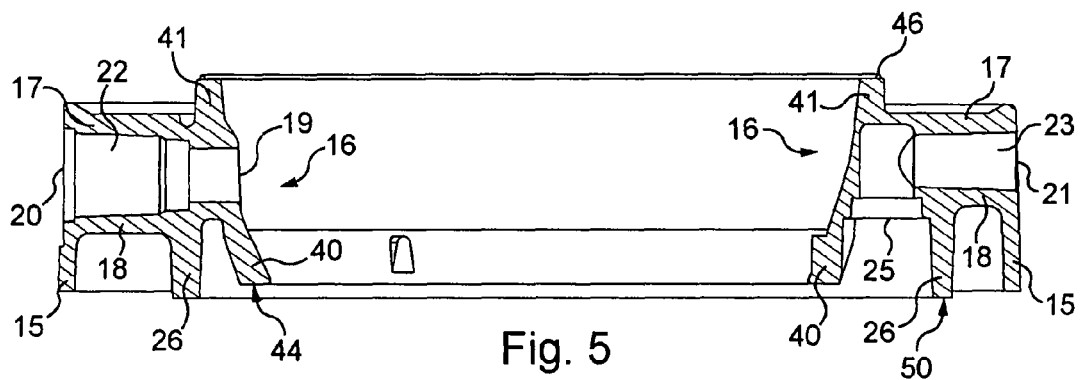
FIG. 5 is a view similar to FIG. 4 but showing a body of the device separately.

The body 2 is molded in one piece from polycarbonate. This body, shown separately in FIG. 5, has an external wall 15 of cylindrical general form and a frustoconical internal wall 16 converging toward the membrane 3.

The wall 15 has two identical depressions 47 and 48 (FIG. 1) obtained by local deformation of the wall.

The walls 15 and 16 are joined together by walls 17 and 18. The wall 16 has an aperture 19 between the greatest diameter portion 41 of the wall 16 and its smallest diameter portion 40.

The aperture 19 communicates by a passage 22 between the walls 17 and 18 with an aperture 20 in the cylindrical wall 15.

A second aperture 21 in the wall 15 diametrically opposite the aperture 20 is extended by a passage 23 between the walls 17 and 18. The passage 23 includes an elbow portion such that, at the opposite end from the aperture 21, it opens into the space situated between the walls 16 and 15 via an aperture 25 in the wall 18.

A cylindrical intermediate wall 26 disposed between the walls 15 and 16 and projecting on the opposite side from the passages 22 and 23 is joined transversely to the wall 18.

The valve 8 is nested inside the passage 22 adjacent the wall 16, being centered about its flange 28 with its flange 28' in abutment with the body 2.

In the same way, the valve 9 is nested in the passage 23, being centered about its flange 29, with its flange 29' in abutment with the portion of wall 18 around the opening 25.

A depression 13 (FIG. 6) in this wall 18 runs along the nested valve 9, forming a vent allowing air to pass between the interior and the exterior of the device, even if the valve 9 (not shown in FIG. 6) is closed.

The valves 8 and 9 are set to open only beyond a certain pressure value when a fluid is supplied under pressure in the flow direction from the inlet aperture 20 to the outlet aperture 21 and to remain closed otherwise.

When the valve 8 has been inserted, the insert 10 is nested inside the passage portion 22 situated at the same end as the aperture 20, centered around its flange 27, with its annular flange 27' coming into abutment with the external surface of the cylindrical wall 15 so that the aperture 12 of the insert, at the opposite end from the valve 8, is situated in the vicinity of the aperture 20 in the body 2.

Here the insert 10 is a Luer female connector, a seal being obtained between this connector and the body 2 by ultrasound welding around the perimeter of the insert.

Like the insert 10, the passage 23 and the walls around it also form a Luer female connector.

Each of the apertures 12 and 21 is closed by a peelable flexible plastic material tongue (not shown) to ensure the integrity of the passages 22 and 23 by protecting them from the air external to the device, which is a potential source of microbiological contamination.

The flexible plastic material cover 7 is forcibly nested from the portion 41 side of the frustoconical wall 16.

The body 2 also includes a pointed annular rib 46 on the edge of the frustoconical portion 41 facing outwardly from the device and adapted to provide a seal with the cover (see below).

The cover 7 shown in FIGS. 1 to 4 is of polypropylene and includes a closure wall 30, an annular hinge 31, a cylindrical nesting strip 32 and an annular flange 33.

The closure wall 30 is connected by the annular hinge 31 to the cylindrical nesting strip 32 and to the flange 33.

In its position nested against the frustoconical wall portion 41, the cylindrical strip 32 bears against the external surface of that portion through the intermediary of an annular rib 34.

The annular hinge 31 connecting the wall 30 to the remainder of the cover has thinner portions 31' and 31" allowing the cover 7 to flex.

The 55 mm diameter membrane 3 is of cellulose ester (it can equally be made of polycarbonate or PVDF). In particular, this material makes it possible to have micro-porosity allowing liquids to pass through but retaining the different microorganisms that they contain.

The periphery of this membrane is sealed to the edge 44 of the frustoconical wall portion 40, this portion forming an annular rim.

Figure 6:
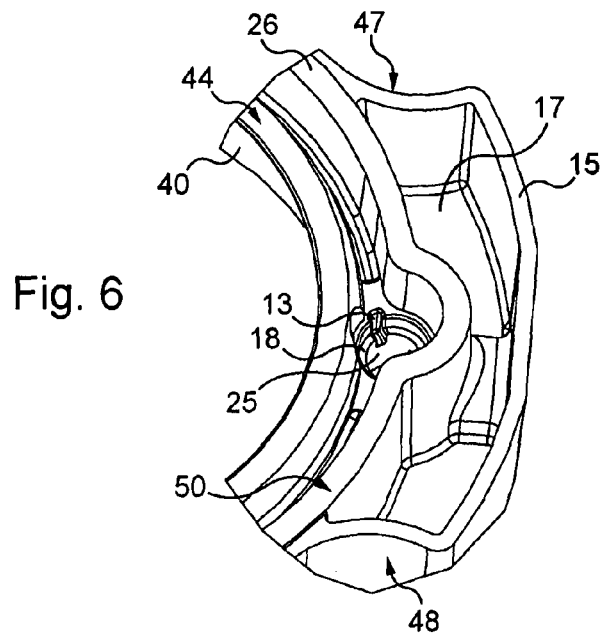
FIG. 6 is a partial perspective view of this body from below, from the side seen on the right in FIG. 5.

Under this membrane is disposed the porous disk-shaped sintered member 4, which has a diameter larger than that of the membrane and thus is disposed against the rim 40 while projecting beyond that rim and supporting the membrane over the whole of its surface 3" (FIGS. 3 and 6).

The sponge disk 5 centered relative to the edges of the sintered member is disposed under the sintered member.

This sponge is of polyvinylacetate (PVA), a hydrophilic plastic having an aerated structure and conventionally used for the manufacture of sponges.

The porous sintered member 4 is supported via the sponge disk 5 by a polyethylene film 6 sealed to the annular edge 50 of the cylindrical wall 26, so that this film entirely covers and hermetically seals the sponge disk 5, the porous sintered member 4 and the membrane 3, with the sponge disk 5 holding the sintered member 4 in position against the membrane 3 and the annular rim 40.

Strips of this film (not visible in the Figures) are sealed to the sintered member 4 to fasten together the film, the sintered member and the sponge disposed between them.

The test device ready for use (with the cover 7 nested in the body 2 and the film 6 sealed to that body) therefore has two flexible and detachable transverse walls (the wall 30 associated with the hinge 31 and the film 6), of which the general disposition is parallel to each other, closing the top and the bottom of the filtration chamber delimited by the body 2, the wall 30 (respectively the film 6) having a face 38 (respectively 39) facing outwardly from the device.

The wall 30 and the film 6 are held by simple adhesion phenomena (by friction as a result of force-fitting in the case of the wall 30, thanks to the strip 32 and the rib 34, and by hermetic bonding or sealing in the case of the film 6).

As explained hereinafter, the cover 7 more precisely closes a receiving volume 43 for the liquid situated between the membrane 3, the frustoconical wall 16 and the cover, and the plastic film 6 partially delimits with the membrane 3 a drainage volume 45 for the liquid situated under the membrane and including the space situated between the membrane and the film 6. This volume communicates with the annular volume 49 situated between the wall portion 40 and the wall 26 forming a volume through which, as will be seen below, the liquid passes (after it has been received in the receiving volume 43 and then drained into the drainage volume 45) so that the liquid is guided to the outlet aperture 21 by the passage 23.

This device, sterilized beforehand by means of gamma radiation, is packaged in a plastic sachet (not shown) consisting of two thermoplastic sheets joined together by a weld bead, a section of that weld bead being peelable by hand.

The clamp 60 is described next with reference to FIGS. 8 to 10.

The clamp 60 includes a mobile plate 61, two fixed plates 62 and 65, a knob 64, a clamping mechanism 63 and two walls 66 and 67.

Figure 8:
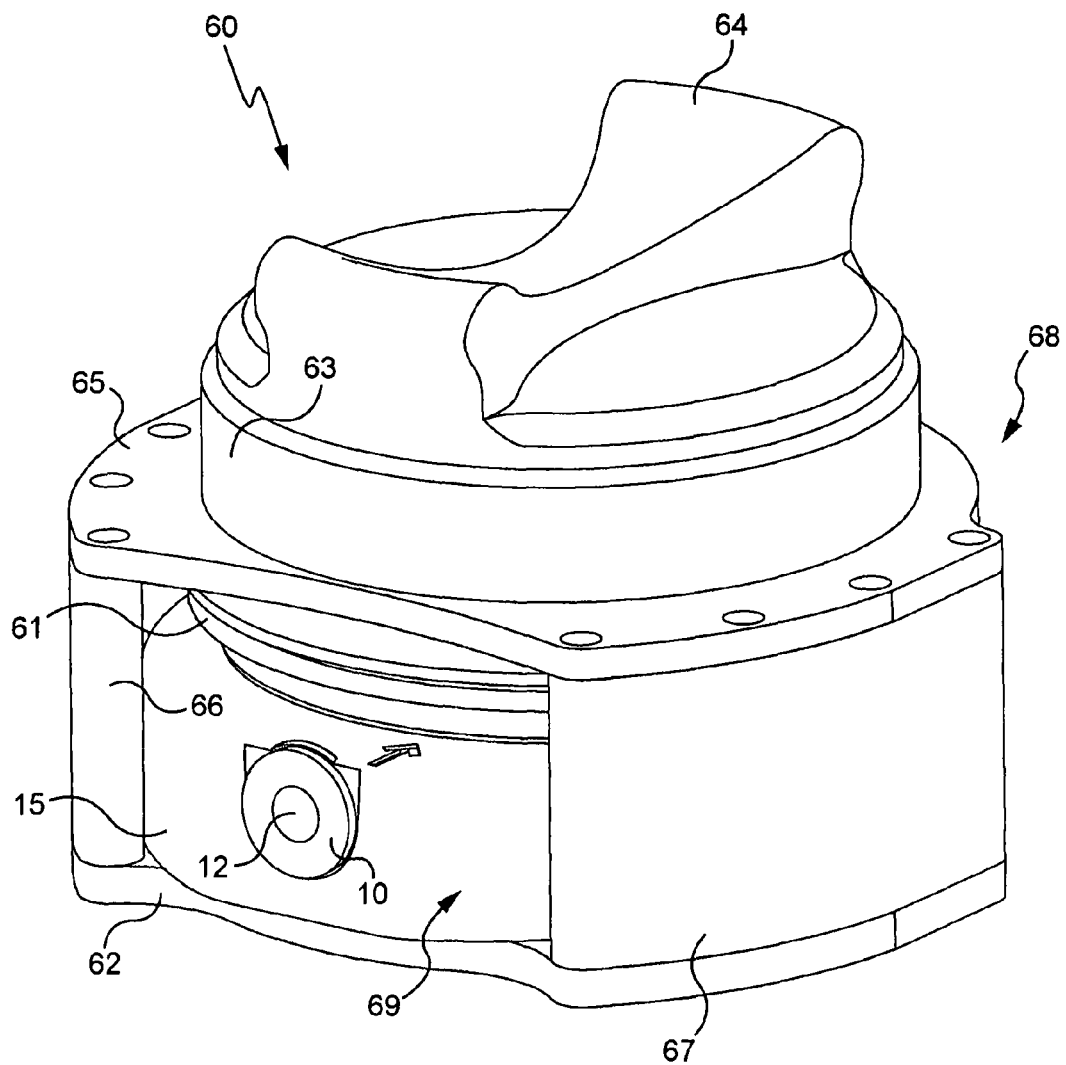
FIG. 8 is a perspective view showing a clamp into which the device has been introduced to be clamped therein in the manner of a vise.

Each of the fixed plates 62 and 65 is mounted against a respective edge of the walls 66 and 67, which are spaced from each other with the result that the clamp 60 has a first window 68 between the walls 66 and 67 and the plates 62 and 65, at the rear in FIG. 8, and a second window 69 at the front in that Figure.

Figure 9:
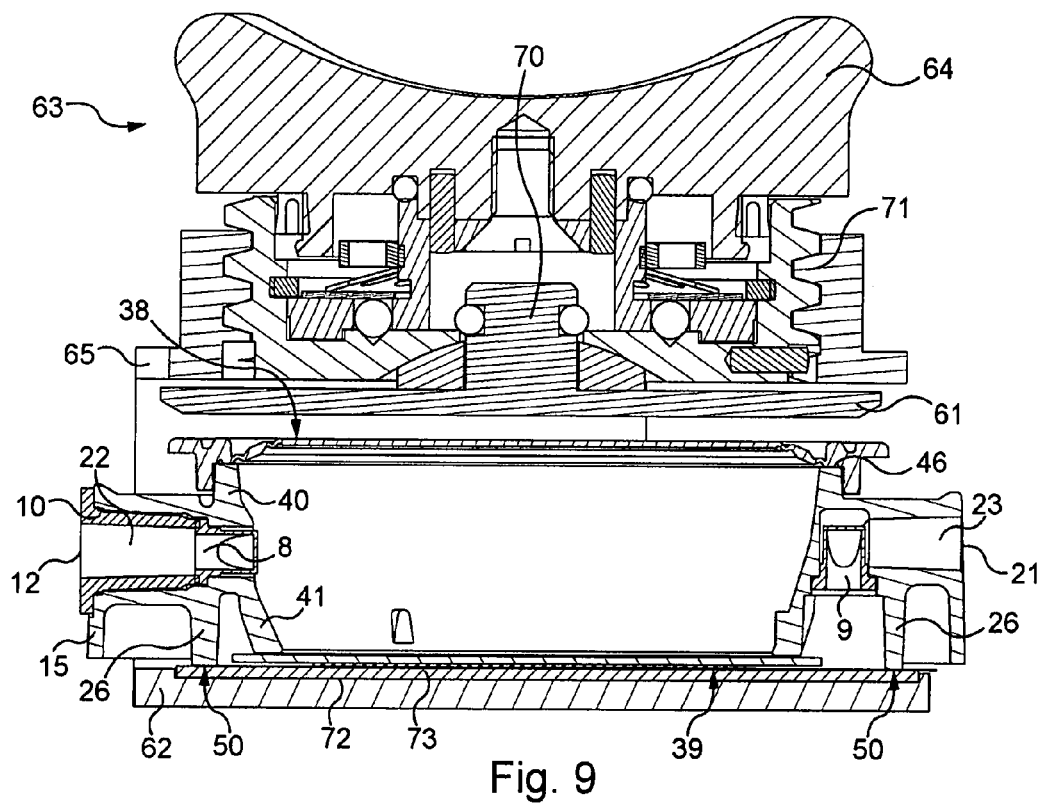
FIGS. 9 and 10 are two elevation views in section of the device engaged in the clamp, respectively showing the clamp in a position in which a mobile clamping plate of the clamp is away from the device and a position in which that plate is clamped against the device.
Figure 10:
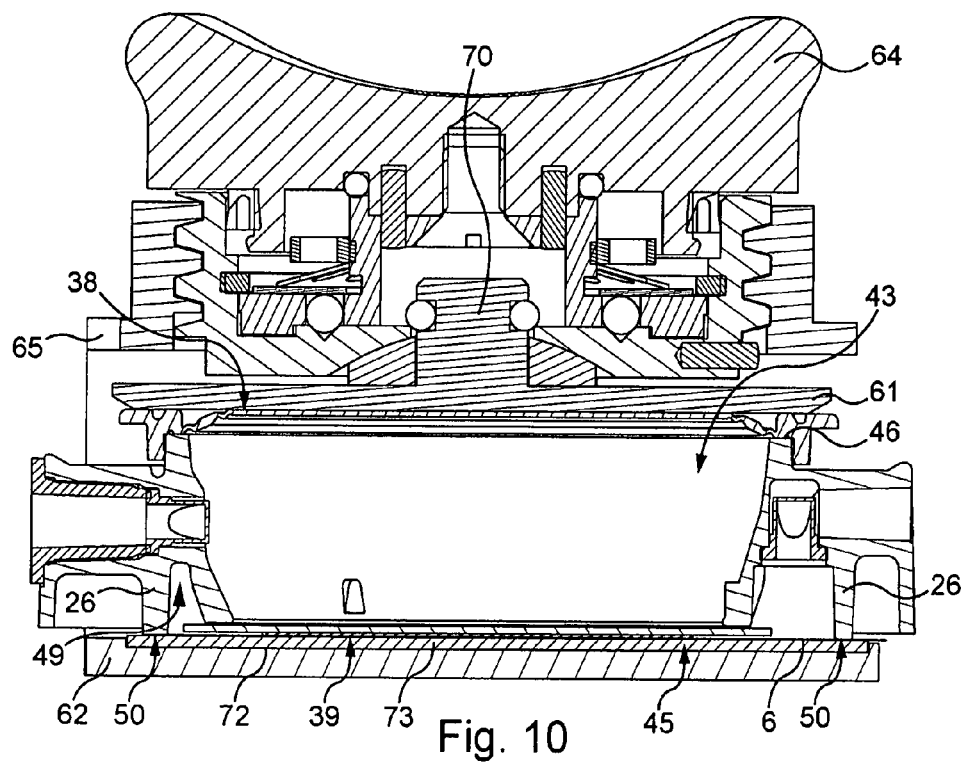

The mobile plate 61 is disposed between the plates 62 and 65 and is connected to the mechanism 63 by a rod 70 passing through an aperture in the plate 65 (FIGS. 9 and 10).

The fixed plate 62 has at its center, on the side facing the plate 65, a cylindrical cavity 72 in which is deposited an elastic and flexible material 73 such as silicone.

The clamping mechanism 63 is connected by a screw to the knob 64 and includes a toothed rack 71 adapted to move the mobile plate 61 in translation between the plates 62 and 65 when an operator manipulates the knob 64 and to hold this plate in position despite any pressure forces exerted on it, for example by the device 1 (see below).

The mechanism 63 is a torque limiter mechanism enabling the device 1 to be clamped with a predetermined force.

How a microbiological test is carried out using a device of the invention is described next.

Initially, the operator opens the individual sachet in which the device 1 is contained (by pulling the two thermoplastic films apart at the peelable weld bead) to extract it by gripping the depressions 47 and 48 of the body 2.

The device 1 is then engaged in the clamp 60 via the window 68, aperture 12 first, so that it comes into abutment against the wall portions 66 and 67 situated in the vicinity of the window 69, which is narrower than the window 68.

Thus the device 1 is disposed between the fixed plate 62 and the mobile plate 61 with the edge 50 of the wall 26 to which the film 6 is sealed bearing on the silicone 73 filling the cavity 72 in the plate 62 (FIGS. 9 and 10).

The operator then manipulates the knob 64 to operate the clamping mechanism 63 and clamp the device 1, the mobile plate 61 coming to bear against the surface 38 of the cover 7 and the fixed plate 62 coming to bear against the surface 39 of the film 6.

When the device 1 is clamped sufficiently tightly, the torque limiter of the mechanism 63 disengages the knob 64 so that the operator cannot clamp the device 1 more tightly. The torque limiter is set so that the clamping pressure is sufficient to seal the device 1 without crushing it unduly.

The wall 26 deforms the silicone locally to ensure a perfect seal between the wall 26 and the film 6 (FIG. 10).

The seal with the body 2 on the side with the cover 7 is ensured by the annular rib 46, which the clamp 60 presses onto a flexible portion of the cover 7.

Once the device has been clamped, the operator peels off the plastic film (not shown) closing off the inlet aperture 12 of the device and then, through the window 69, connects the Luer female inlet connector 10 of the device to a male Luer connector (not shown) connected to a filling passage communicating via a valve (not shown) with a tank of liquid under pressure (not shown).

The operator then peels off the plastic film closing off the outlet aperture 21 to connect the outlet female Luer connector to a drainage passage (not shown) through the window 68.

The operator then maneuvers the valve so that the filter chamber is at the same pressure as the liquid, for example 3 bar. The clamp 60 ensures that the device 1 is sealed for pressures as high as 8 bar.

Figure 4:
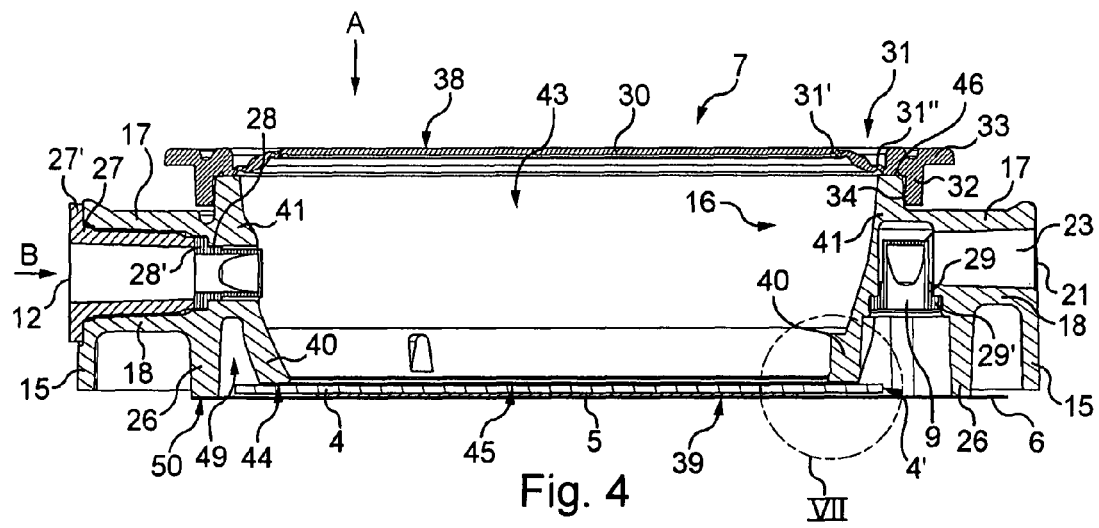
FIG. 4 is an elevation view of the device in section taken along the line IV-IV in FIG. 3.

The liquid then passes through the passage 22 in the direction of the arrow B (FIG. 4), its pressure being sufficient to open the valve 8, and then fills the receiving volume 43 and begins to pass through the entire thickness of the membrane 3 in the axial filtering direction represented by the arrow A (FIG. 4).

Because this membrane is hermetically sealed to the edge 44 of the rim 40, the liquid can escape from the receiving volume 43 only by passing through the entire thickness of the membrane 3.

Once the liquid has been filtered through the membrane, it enters the drainage volume 45 in the porous sintered member 4 and passes at least partially through the latter.

Figure 7:
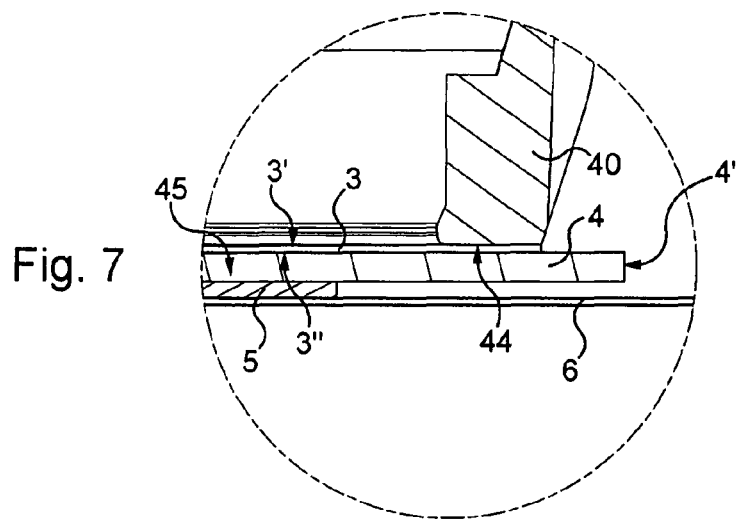
FIG. 7 is a view to a larger scale of the detail VII in FIG. 4.

The major portion of the liquid passes through only a portion of the thickness of the sintered member, escaping from that member via its edge 4' (FIG. 7).

The drainage volume is therefore essentially localized within the volume occupied by the sintered member 4 and within the volume extending radially (i.e. transversely relative to the axial filtration direction) around the sintered member situated in the vicinity of the edge 4'.

The liquid then moves from the drainage volume 45 toward the transit volume 49 situated between the rim 40 and the wall 26 radially distributed around the membrane 3, and the liquid is therefore conveyed to the valve 9.

Like the valve 8, this valve is adapted to open at the working pressure of the device, and the liquid can therefore be evacuated via the aperture 21, flowing through the passage 23.

Should the operator interchange the inlet and outlet apertures by mistake, the check valves 8 and 9 prevent the liquid from passing through the device in the direction that would cause a pressure difference across the membrane 3 that would deform it on the opposite side to the sintered member supporting it and possibly tear it.

Once all of the liquid has been filtered, the operator closes the liquid inlet valve, disconnects the filler and drain passages of the device 1 and extracts the device 1 from the clamp 60. With the device extracted from the clamp, the membrane 3 charged with water is supported only by the sintered member 4, to prevent it tearing.

The operator then purges the liquid contained in the device by connecting the outlet aperture 21 of the device to a vacuum pump to apply a reduced pressure via the passage 23 to aspirate the liquid.

Most of the liquid contained in the receiving volume 43, drainage volume 45 and transit volume 49 is evacuated via the outlet aperture 21 to the vacuum flask and is replaced by sterile air (when working under an air flow hood, for example) that penetrates the device via the valve 8 that opens.

Figure 11:
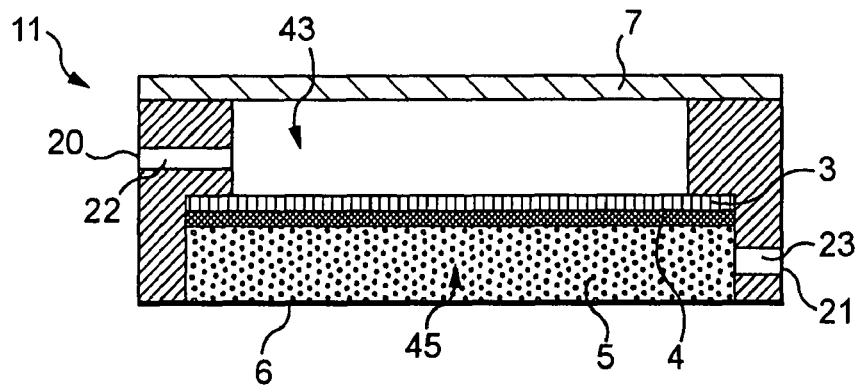
FIGS. 11 to 13 are three schematic views of the microbiological test device during purging of the device.
Figure 12:
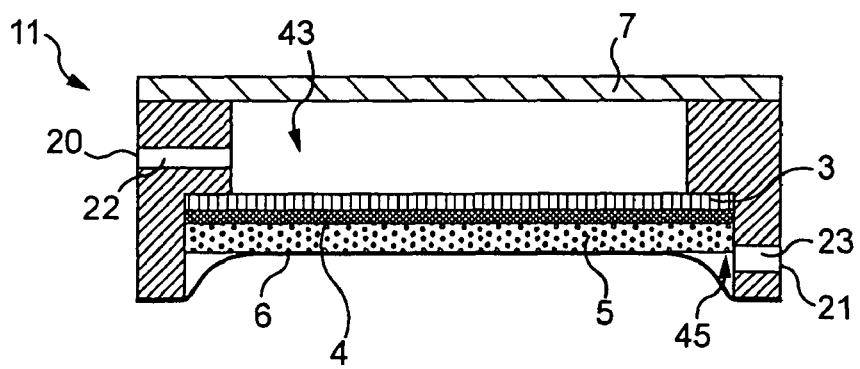
Figure 13:
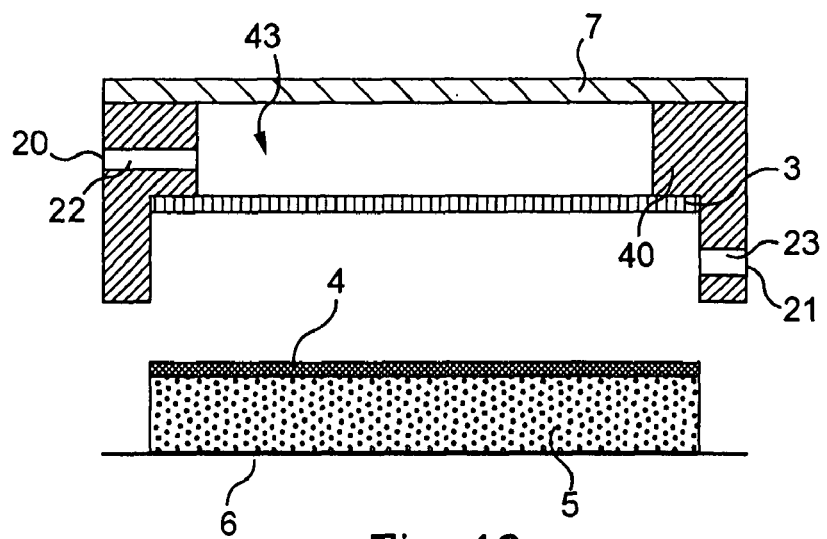

To simplify the explanation, the remainder of the purging operation is explained with the aid of FIGS. 11 to 13 which represent the device 1 highly schematically.

As explained above, when most of the liquid has been purged (FIG. 11), the surfaces of the membrane are brought into contact with air that has entered the device.

The bubble point phenomenon means that no gas bubbles can escape from the wetted membrane, which makes the membrane airtight, preventing any flow of liquid or gas toward the outlet aperture 21.

In response to this pressure reduction, the pressure external to the device then causes deformation of the peelable film 6, which moves toward the porous sintered member 4 and the membrane 3.

Consequently, the deformed peelable film 6 squeezes the disk-shaped sponge 5 against the sintered member 4 as shown in FIG. 12, with the result that this sponge, squeezed by the film 6 in this way, is partially emptied of the liquid that it absorbs during filtration.

Once the sponge has been squeezed, aspiration is stopped. The vent 13 (FIG. 6) beside the valve 9 of the device allows sterile air to pass through so that the pressure inside the device becomes equal again to the exterior pressure, with the result that the film 6 returns to its initial position and the sponge 5, which is relatively elastic and (in the absence of any reduced pressure) released from the force exerted by the peelable film 6, returns substantially to its initial volume (FIG. 11) without being saturated with water, since some of the liquid that it held has been purged by squeezing it.

Consequently, when the sponge 5 resumes its volume it simultaneously absorbs any residual liquid still contained in the device and in particular the liquid still present in the pores of the membrane 3 and in the regions neighboring the preferential flow paths.

A plurality of cycles of this type in which a reduced pressure is applied followed by a return to the external pressure (so as to squeeze the sponge repeatedly in the manner of a pump) may be carried out to make purging even more effective.

When this purging operation has been completed, the operator grasps the peelable film 6 near one of the depressions 47 and 48 and peels the film off (FIG. 1), the sponge disk 5 and the porous sintered member 4 being entrained (FIG. 13) by the film 6 (the film being sealed to the sintered member at several places), and removed with it, only the membrane 3 remaining fastened to the rim 40.

The face 3" of the membrane is therefore rendered accessible and can be applied to the surface of a gel growth medium adapted to be brought into contact with the membrane (having a convex surface, for example).

The device brought into contact with the gel growth medium is then left in an incubation chamber to incubate for the time necessary for microorganisms retained in the membrane 3 so to grow that they become visible and can be counted.

To count the colonies when incubation has been completed, either the colonies are counted through the cover if it is transparent or the cover 7 is removed and the colonies counted directly.

Instead of growth on a gel medium, it is equally possible to effect fast detection of microorganisms by spraying onto the membrane 3 (after removing the cover 7) one or more reagents revealing the presence of the ATP of the microorganisms by luminescence (after making that ATP accessible, for example by chemical or microwave lysis of the microorganisms), for example.

In a variant that is not shown, the cavity 72 in the fixed plate 62 has a maximum dimension less than the diameter of the wall 26 with the result that the surface 50 of this wall bears against the plate 62 outside the cavity 72, this cavity remaining empty to enable the film 6 to deform locally into the cavity in response to the pressure during filtration, moving away from the membrane 3 and the sintered member 4 to facilitate the flow of the fluid from the drainage region to the transit region, the drainage volume being in this case also formed of the volume situated between the porous sintered member 4 and the film 6 deformed by the pressure of the liquid.

At the end of the filtering operation the film 6 returns elastically to its initial position to hold the sintered member 4 and the sponge 5 in position.

In another variant that is not shown, the passage 22 is blocked and the liquid is introduced into the receiving volume by removing the cover 7 and/or the porous sintered member 4 is dispensed with in favor of a single disk-shaped sponge 5 thick enough to support the membrane 3 and to enable it to resist the filtration pressure.

In a further variant (not shown), the porous sintered member is recessed annularly into the body 2 of the device and/or the envelope 11 has no vent for returning the device to atmospheric pressure after aspirating the liquid, so that it is only when the film 6 is peeled off that the sponge returns to its initial volume and simultaneously absorbs the residual liquid.

Figure 14:
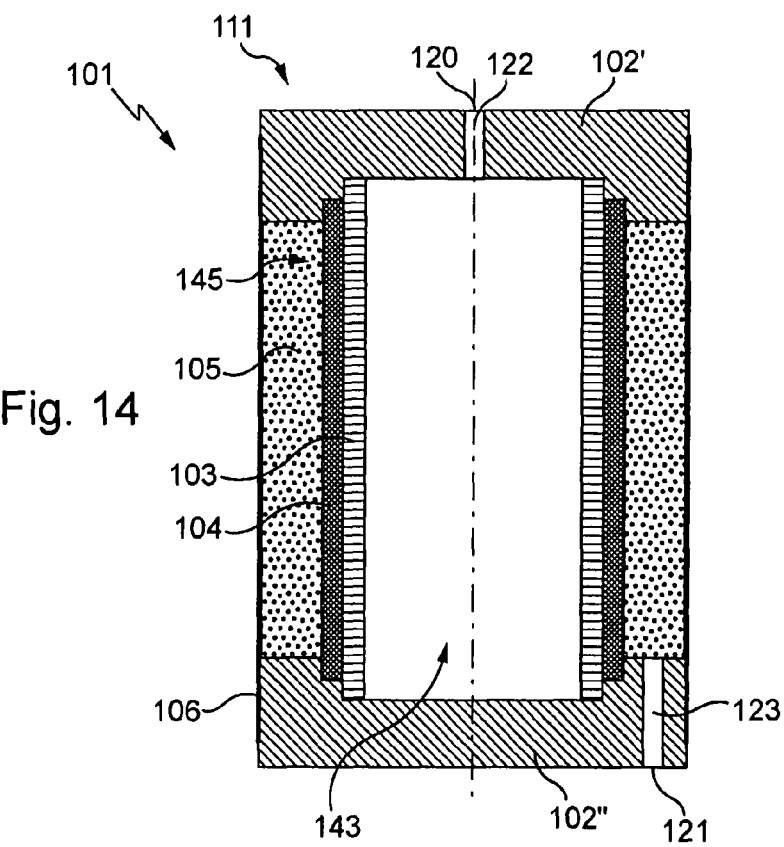
FIGS. 14 and 15 are two views similar to FIGS. 11 and 12 for a second embodiment of the device.
Figure 15:
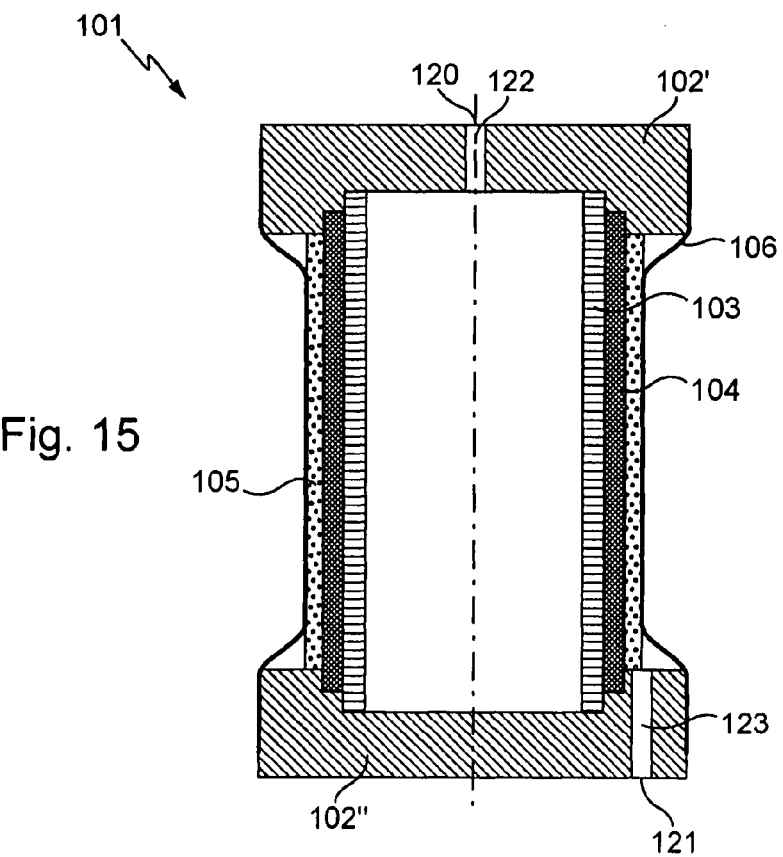

FIGS. 14 and 15 show another embodiment.

Generally speaking, the same reference numbers increased by 100 are used for similar elements.

The filter device 101 includes an envelope 111 formed of a stopper 102' and a stopper 102" facing each other and a peelable film 106.

A centered filler passage 122 is formed in the stopper 102' and a purge passage 123 is formed at the periphery of the body 102". Between the bodies 102' and 102" there are disposed, at decreasing distances from the passage 122, a cylindrical sponge 105, a cylindrical porous sintered member 104 and a membrane 103 of closed contour (here cylindrical). The surface of the sponge 105 on the side opposite the sintered member 104 is entirely covered by the cylindrical peelable film 106.

The film 106 also surrounds part of the peripheral surface of the stoppers 102' and 102".

The receiving volume 143 is delimited by the stoppers 102' and 102" and the membrane 103, and the drainage volume 145 is delimited by the member 103 and the film 106.

During the purging phase, aspiration causes the liquid to flow through the passage 123 until the cylindrical membrane 103 becomes airtight, with the result that the cylindrical film 106 is deformed to squeeze the sponge 105 against the cylindrical sintered member 104, thereby purging some of the liquid contained in the sponge through the passage 123.

When the pressure returns to normal, the sponge 105 resumes its initial volume and absorbs the residual liquid contained in the device 101.

The film 106 is then peeled off, after which the sponge 105 and the sintered member 104 are removed in order to spray onto the membrane 103 one or more reagents for fast detection of microorganisms collected on the membrane (for example by bioluminescence).

In a variant that is not shown the membrane 103 and the film 106 of the device 101 are replaced by a pleated film (with a closed star-shaped contour, for example) to increase the area of exchange of the membrane with the liquid.

Whatever the embodiment of the device, the operation of squeezing the sponge makes it possible to expel the excess water with high efficiency such that the step of detecting microorganisms is facilitated in particular when the detection is carried out by measurement of luminescence, the quality of the signal measured on the membrane with a low charge of water being greatly improved (in terms of intensity and contrast, in particular).

Furthermore, the possibility of repeated performance of the operations of placing the device under reduced pressure and of the ceasing of that reduced pressure makes it possible to purge the liquid contained in the device very efficiently by expelling it from the sponge in the manner of a pump.

The efficient purging of the liquid thus makes it possible for example to successively pass several different liquids into the device after the liquid to analyze, such as a rinsing liquid (to eliminate for example the antibiotics that may possibly be contained in the liquid to analyze and able to slow the growth of the microorganisms), a nutritive liquid (for placing the device directly in incubation without having to make it cooperate with a gel growth medium cassette), or a liquid including a reagent adapted to reveal the presence of microorganisms by luminescence and/or a lysing agent (to perform the analysis without having to spray the reagent on the membrane after peeling the film).

Between each passage of liquid, the operation of purging the liquid (possibly by pumping by repeated placing under reduced pressure and ceasing of the reduced pressure) makes it possible to keep a membrane with a low level of impregnation and thus avoid any risk of dilution and interaction between the liquids successively absorbed by the membrane.

The present invention is not limited to the embodiment described and shown and encompasses any variant execution thereof.

The invention claimed is:

1. Device for microbiological testing of a sample of liquid flowing under pressure, including an envelope and a filter membrane inside said envelope, said membrane subdividing the internal volume of said envelope into a liquid receiving volume communicating with an inlet aperture and into a liquid drainage volume communicating with an outlet aperture, said envelope including a removable body and, inside said drainage volume, a support for supporting said membrane when wetted;

wherein:
said support include includes a relatively absorbent and flexible sponge; and
said removable body includes a flexible wall disposed against said sponge, said flexible wall being adapted to be moved toward said membrane when said device is subjected to a reduced pressure inside said drainage volume and to return to its initial position when said reduced pressure ceases.

2. Device according to claim 1, wherein said support also include a porous sintered and relatively rigid member disposed between said membrane and said sponge.

3. Device according to either claim 1 or claim 2, wherein said sponge is of polyvinylacetate.

4. Device according to claim 1, wherein said removable body of said envelope is formed of said flexible wall.

5. Device according to claim 1, wherein said flexible wall is a peelable film.

6. Device according to claim 5, wherein said film is of polyethylene.

7. Device according to claim 1, wherein said flexible wall holds said support in position inside said envelope.

8. Device according to claim 1, wherein said flexible wall is sealed to said support.

9. Device according to claim 1, wherein said device includes a first calibrated valve disposed between said inlet aperture and said receiving volume and a second calibrated valve disposed between said drainage volume and said outlet aperture, said valves being adapted to open in the direction of flow from said inlet aperture to said outlet aperture.

10. Device according to claim 1, wherein a vent adapted to allow air to pass between the interior and the exterior of said envelope is formed in said envelope.

11. Device according to claim 1, wherein said membrane, said sponge and said peelable film have closed contours.

12. Assembly for microbiological testing of a sample of liquid flowing under pressure including a device according to claim 1 and a clamp having clamping means adapted to hold said device in the manner of a vise by said flexible wall.

13. Assembly according to claim 12, wherein said clamp has a fixed plate and a plate mobile between a rest position in which it is away from the device and a clamping position in which it bears against said device.

14. Assembly according to claim 13, wherein the plate that bears on said flexible wall has a central cavity and in that said flexible wall of said device is also adapted to move away from said membrane within said cavity when said device is subjected to an increased pressure in said drainage volume and to return to its initial position when said increased pressure ceases.

15. A method for the microbiological testing of a sample of liquid flowing under pressure including:
   a) the step of obtaining a device according to claim 1;
   b) the step of passing said sample between the inlet aperture and the outlet aperture of said device;
   c) the step of subjecting said device to a reduced pressure within the drainage volume of said device;
   d) the step of making said reduced pressure cease; then
   e) the step of detecting the presence of microorganisms on the membrane of said device.

16. A method according to claim 15, further comprising, prior to step e), the step of passing a rinsing liquid between the inlet aperture and the outlet aperture of said device and then the implementation of steps c) and d) again.

17. A method according to any one of claim 15 or 16, further comprising, prior to step e), the step of passing a nutritive liquid between the inlet aperture and the outlet aperture of said device and then the implementation of steps again.

18. A method according to any one of claim 15 or 16, further comprising, prior to step e), the step of passing between the inlet aperture and the outlet aperture of said device a liquid adapted to reveal the presence of microorganisms by luminescence and then the implementation of steps c) and d) again.

19. A method according to any one of claim 15 or 16, further comprising, prior to step e), the step of repeating steps c) and d) at least once.

* * * * *